United States Patent [19]

Mendoza

[11] Patent Number: 4,654,447

[45] Date of Patent: Mar. 31, 1987

[54] PROCESS FOR THE PREPARATION OF TRIBROMOTETRAMETHYLBIPHENOL AND RELATED COMPOUNDS

[75] Inventor: Abel Mendoza, Midland, Mich.

[73] Assignee: The Dow Chemical Company, Midland, Mich.

[21] Appl. No.: 831,400

[22] Filed: Feb. 20, 1986

[51] Int. Cl.[4] .............................................. C07C 39/12
[52] U.S. Cl. .................................. 568/730; 568/723; 568/726
[58] Field of Search ....................... 568/730, 723, 726

[56] References Cited

U.S. PATENT DOCUMENTS

| | | | |
|---|---|---|---|
| 3,929,908 | 12/1975 | Orlando et al. | 568/730 |
| 3,956,403 | 11/1976 | Orlando et al. | 568/730 |
| 4,058,570 | 11/1977 | Kinson et al. | 568/730 |

OTHER PUBLICATIONS

*JFF/Fire Retardant Chemistry*, v. 2, pp. 183–193 (1975).
P. L. Kinson et al., *Journal of Applied Polymer Science*, v. 23, pp. 155–162 (1979).

*Primary Examiner*—Werren B. Lone

[57] ABSTRACT

Prepare 3,3′,5-tribromo-2,2′,6,6′-tetra(primary alkyl)-1,1′-biphenol in high yields by contacting a 3,3′,5,5′-tetra-substituted diphenoquinone and a brominating agent under proper reaction conditions.

16 Claims, No Drawings

PROCESS FOR THE PREPARATION OF TRIBROMOTETRAMETHYLBIPHENOL AND RELATED COMPOUNDS

BACKGROUND OF THE INVENTION

The present invention relates to the bromination of cyclic compounds.

Various observations have been made by the prior art regarding reactions between bromine and 3,3',5,5'-tetra-substituted diphenoquinone carried out in both the presence and the absence of inert liquid solvents. For example, U.S. Pat. No. 3,929,908 discloses the bromination of 3,3',5,5'-tetra-substituted diphenoquinones in the absence of any inert diluent at about ambient room temperature (25° C.) while cooling the reaction media and controlling the rate of addition of the diphenoquinone so as to avoid an uncontrolled exothermic reaction. Said process requires large excesses of bromine in order to maintain a liquid reaction mixture, and produces 3,3',5,5'-tetrabromo-2,2',6,6'-tetra-substituted-4,4'-biphenol (TTB). The use of large excesses of bromine is disadvantageous in many ways. For example, the use of large excesses of bromine can give products which contain undesirably large amounts of occluded bromine. Example 7 of the patent discloses the preparation of 3,3',5-tribromo-2,2',6,6'-tetramethyl-p,p'-biphenol (Tri-TB) with a selectivity of 76 percent as determined by gas chromatograph; the calculated yield is approximately 62 percent.

U.S. Pat. No. 4,058,570 discloses a process for the preparation of TTB wherein bromine is added to a 3,3',5,5'-tetra-substituted diphenoquinone none (TSDQ) at a temperature of less than 20° C. in the presence of a liquid diluent, then evolving HBr at a temperature of at least about 15° C., heating the resulting reaction mixture at elevated temperatures to complete the bromination reaction, and recovering TTB in a yield of at least 70 percent. The patent teaches that molar $Br_2$:TSDQ ratios of 6.5:1 are operable, but prefers ratios of 15:1 or higher. The patent does not disclose the production of Tri-TB.

Polybrominated tetra-substituted biphenols have several uses, many examples of which are listed in the patents cited hereinabove. For example, said biphenols can be employed as flame-retardant additives for resinous materials, and can be copolymerized to give flame-retardant polymers which can be readily formed into films, sheets, fibers, laminates, etc. However, TTB is poorly soluble in many organic solvents, and therefore is difficult to handle in certain applications. As stated in *JFF/Fire Retardant Chemistry*, V. 2, pp. 183–193 (1975), the solubility of TTB in acetone at 25° C. is only 3.2 g per 100 cc of solvent.

In view of the deficiencies of TTB and the prior art processes for its preparation, it would be desirable to have a process which could produce in high yield a polybrominated tetra-substituted biphenol having increased solubility in organic solvents, and which could be operated without requiring large excesses of bromine.

SUMMARY OF THE INVENTION

The present invention is such a process for the preparation of tribrominated tetra-substituted biphenols in high yield. More specifically, the present invention is a process comprising contacting a 3,3',5,5'-tetra(primary alkyl)diphenoquinone and a brominating agent under reaction conditions such that the corresponding 3,3',5-tribromo-2,2',6,6'-tetra(primary alkyl)biphenol is produced in a yield of at least about 70 percent.

The process of the present invention is advantageous in that it does not require large excesses of bromine, and in that it unexpectedly produces a high yield of the desired Tri-TB product. Surprisingly, the Tri-TB product has increased solubility compared to TTB.

Detailed Description of the Invention

The tetra-substituted diphenoquinones which are useful as starting materials in the process of the present invention are known compounds, and are described in U.S. Pat. Nos. 3,929,908; 3,956,403; and 4,058,570. The teachings of said patents regarding 3,3',5,5'-tetra-substituted diphenoquinones are incorporated herein by reference. Preferably, the diphenoquinone starting material is substituted with primary alkyl or primary lower alkoxy moieties, with primary alkyl being more preferred. Preferred alkyl moieties are lower alkyl of from 1 to about 6 carbon atoms, with methyl being most preferred. The four substituents of the tetra-substituted diphenoquinones can be the same or different, but it is preferred that they be the same.

A brominating agent is employed in the practice of the present invention. While it may be possible to employ known brominating agents which are useful for the bromination of diphenoquinone rings, bromine is the preferred brominating agent. In contrast to prior art processes for the high yield production of polybrominated tetra-substituted biphenols, the process of the present invention requires only from about 4 to about 5 moles of bromine per mole of diphenoquinone starting material. If a brominating agent is employed which is not bromine, the amount of said agent to be employed should provide bromine in the quantities stated hereinabove.

A reaction medium is advantageously employed in the process of the present invention. Any essentially nonreactive liquid can be employed as the reaction medium providing that bromine and the reaction medium form at least a partially miscible liquid phase. Any amount of diluent can be employed so long as the desired yield is obtained. Preferably, the amount of diluent employed is such that the molar concentration of bromine in the reaction mixture is from about 3.5 to about 4.5. Preferred reaction media include essentially nonreactive halogenated hydrocarbons, such as relatively low boiling halogenated aliphatic hydrocarbons, e.g., carbon tetrachloride, methylene chloride, chloroform, bromochloromethane, bromotrichloromethane, trichloroethane, and the like, as well as mixtures of these compounds. It is especially preferred to employ methylene chloride or carbon tetrachloride as the reaction medium.

According to the process of the present invention, a TSDQ and a brominating agent are contacted, preferably in the presence of a reaction medium. Preferably, the brominating agent is added to a mixture comprising a TSDQ and a reaction medium. As stated hereinabove, the addition is conducted in a manner such that the molar concentration of bromine in the reaction mixture is from about 3.5 to about 4.5. When the addition of the brominating agent is completed, the resulting reaction mixture typically is brought to an elevated temperature until the reaction is completed.

The addition temperature, i.e., the temperature of the reaction mixture during the period of addition of the brominating agent thereto, typically is about 20° C. or lower. Preferably, the addition temperature is about 10° C. or less. Most preferably, the addition temperature is from about 6° C. to about −15° C.

When the addition of the brominating agent to the reaction mixture is completed, the total reaction mixture may be heated to elevated temperature in order to assure complete reaction. Typically, the total reaction mixture is heated to reflux temperature and said temperature is maintained until the reaction is complete. Preferably, the elevated temperature is from about 40° C. to about 70° C. Completion of the reaction may be observed by following the rate of evolution of hydrogen bromide from the reaction mixture, i.e., the reaction is complete when the rate of hydrogen bromine evolution falls to zero. Ordinarily, the reaction will proceed at atmospheric pressure or higher, but subatmospheric pressure may be employed if desired.

It is desirable to add the brominating agent to the reaction mixture at a sufficiently slow rate to minimize loss of bromine and reaction medium overhead, and to permit the desired low reaction temperature to be maintained under conditions of control and safety. Typically, the reaction system is maintained under anhydrous conditions until such time as the reaction is complete.

A total reaction time of from about 1 to about 6 hours is generally adequate for complete reactions under the conditions of the invention. Typically, a total reaction time of up to about 3 hours will be sufficient to produce high yields.

When the reactants and reaction medium are properly combined under reaction conditions as specified hereinbefore, a 3,3',5-tribromo-2,2',6,6'-tetra-substituted biphenol will be formed in high yield For the purposes of the present invention, the term "high yield" refers to a yield of at least about 70 percent. For the purposes of the present invention, yield is the numerical product of conversion and selectivity, and is defined according to the following equations:

$$\% \text{ yield} = \frac{RBC \times STTB}{\text{wt. of theoretical Tri-}TB \text{ product}}$$

wherein RBC is the weight of recovered brominated compounds and STTB is the percent selectivity to Tri-TB product. The percent selectivity is determined by gas chromatography for the purposes of the preceding formula. Preferably, the yield is at least about 75 percent; more preferably the yield is at least 80 percent; most preferably the yield is at least about 85 percent.

The reaction mixture resulting from carrying out the process of the present invention at low initial reaction temperature can be processed by a variety of known work-up procedures to isolate the products. The teachings of U.S. Pat. No. 4,058,570 regarding recovery techniques are incorporated herein by reference.

Specific Embodiments

The following examples are given to illustrate the invention and should not be construed as limiting its scope.

EXAMPLE 1

Preparation of Tribromotetramethylbiphenol (3,3',5-Tribromo-2,2',6,6'-tetramethylbiphenol)

A 240.3-g portion of 3,3',5,5'-tetramethyldiphenoquinone is suspended in one liter of carbon tetrachloride, and the slurry is cooled to 5° C. with an ice water bath. A 240-ml portion of bromine is added over a period of 10 minutes. After increasing the bath temperature to 10° C., an exothermic reaction takes place which increases the temperature of the reaction mixture to 30° C. over a period of 5 minutes. When the exotherm subsides, the mixture is kept at 20° C. for 0.5 hour; copious evolution of HBr is observed during this period. The mixture is brought to reflux, 65° C., and after refluxing for one hour, the product has the following composition by gas chromatography: 4 percent dibromo, 92 percent tribromo, and 4 percent tetrabromo. After refluxing for one more hour, the excess bromine is removed by distillation with the aid of one liter of fresh solvent. Once the distillate is clear, the slurry is cooled, and the insoluble solid is filtered and dried. A tan solid (446 g) is obtained which, when analyzed by gas chromatography, is 4 percent dibromo, 91 percent tribromo and 5 percent tetrabromo. This corresponds to an 85 percent yield of tribromo based on theoretical. The solid is washed with one liter of water and is dried. It is further purified by slurrying in 1.2 liters of toluene, refluxing for 15 minutes, cooling, and filtering the white solid. After drying at 110° C. for 4 hours, 285 g of white solid is obtained of 97 percent purity, containing 2 percent dibromo and 1 percent tetrabromo. The solid melts at 236° C.-239° C., and has the following HNMR spectrum: HNMR (acetone $d_6$)$\delta$: 2.24 (s, 3H), 2.40 (s, 9H), 6.70 (s, 1H), 7.50 (s, 1H), 7.84 (s, 1H).

EXAMPLES 2-6 AND COMPARATIVE EXPERIMENTS

The procedure of Example 1 is repeated several times except that certain reaction parameters are varied, as indicated in Table I. Results of each run are included in Table I.

TABLE I

| Run | Solvent | $Br_2$[1] Conc. | $Br_2$:$TSDO$[2] | % Selectivity* | % Yield |
|---|---|---|---|---|---|
| C.E. 1 | CCl$_4$ | 6.24 | 4.76 | 13-76-11 | 62 |
| C.E. 2 | CCl$_4$ | 2.17 | 3.50 | 20-80-<1 | 46 |
| C.E. 3 | CCl$_4$ | 2.55 | 4.69 | 11-88-1 | 64 |
| C.E. 4 | CCl$_4$ | 2.91 | 3.28 | 15-84-1 | 67 |
| Ex. 2 | CCl$_4$ | 3.53 | 4.38 | 13-85-1 | 75 |
| C.E. 5 | CCl$_4$ | 3.90 | 4.00 | 7-89-4 | 67 |
| Ex. 3 | CCl$_4$ | 3.90 | 4.69 | 4-91-5 | 85 |
| C.E. 6 | CCl$_4$ | 4.51 | 4.69 | 1-75-24 | 64 |
| C.E. 7 | CCl$_4$ | 4.84 | 5.16 | 3-67-30 | 57 |
| Ex. 4 | CH$_2$Cl$_2$ | 3.90 | 4.69 | 12-82-6 | 83 |
| Ex. 5 | CH$_2$Cl$_2$ | 3.98 | 5.00 | 9-83-8 | 83 |
| Ex. 6 | CH$_2$Cl$_2$ | 4.29 | 5.50 | 10-77-13 | 77 |
| C.E. 8 | EDC | 3.90 | 4.69 | 1-71-28 | 56 |
| C.E. 9 | EDC | 3.32 | 4.00 | 3-94-3 | 67 |

[1]Molar concentration
[2]Molar ratio
*Determined by gas chromatography and listed in the order dibromo - tribromo - tetrabromo.
EDC = 1,2-dichloroethane (ethylene dichloride)
Note:
The entry for Comparative Experiment 1 merely lists information taken from U.S. Pat. 3,929,908.

It can be seen from the preceding examples that the process of the present invention is capable of producing the desired tribromo compound in high yield by advantageously employing only a slight excess of bromine.

What is claimed is:
1. A process for the preparation of a 3,3',5-tribromo-2,2',6,6'-tetra(primary lower alkyl)biphenol, the process comprising adding at a temperature of less than about 20° C. from about 4.2 to about 5.6 moles of bromine per mole of 3,3',5,5'-tetra(primary lower alkyl)diphenoquinone to a mixture comprising an essentially nonreactive halogenated aliphatic hydrocarbon reaction medium and the quinone under reaction conditions such that the molar concentration of bromine in the resulting mixture is from about 3.5 to about 4.5, and then raising the temperature of the resulting mixture to an elevated temperature to complete the bromination reaction to form the 3,3',5-tribromo-2,2',6,6'-tetra(primay lower alkyl)biphenol.

2. The process of claim 1 wherein the reaction medium is methylene chloride.

3. The process of claim 1 wherein the reaction medium is carbon tetrachloride.

4. The process of claim 1 wherein the addition temperature is less than about 10° C.

5. The process of claim 1 wherein the primary alkyl moieties are methyl, the yield is at least about 70 percent, the addition temperature is less than about 6° C., and the reaction medium comprises methylene chloride, carbon tetrachloride, or mixtures thereof.

6. A process comprising contacting a 3,3',5,5'-tetra(primary lower alkyl)diphenoquinone and bromine under reaction conditions such that the corresponding 3,3',5-tribromo-2,2',6,6'-tetra(primary lower alkyl)biphenol is produced in a yield of at least about 70 percent.

7. The process of claim 6 wherein the reaction medium is methylene chloride.

8. The process of claim 6 wherein the reaction medium is carbon tetrachloride.

9. The process of claim 6 wherein the initial contacting temperature is about 20° C. or lower.

10. The process of claim 9 wherein the initial contacting temperature is less than about 10° C.

11. The process of claim 9 wherein the initial contacting temperature is less than about 6° C.

12. The process of claim 6 wherein the molar concentration of bromine in the reaction mixture is from about 3.5 to about 4.5.

13. The process of claim 6 wherein from about 4.2 to about 5.6 moles of bromine are employed per mole of 3,3',5,5'-tetra(primary alkyl)diphenoquinone.

14. The process of claim 6 wherein the yield is at least about 75 percent.

15. The process of claim 6 wherein the yield is at least about 80 percent.

16. The process of claim 6 wherein the yield is at least about 85 percent.

* * * * *